United States Patent

Corby et al.

Patent Number: 5,795,552
Date of Patent: Aug. 18, 1998

[54] APPARATUS FOR HEATING AND VENTING A CONTAINER

[75] Inventors: Kenneth Dean Corby, Rochester; David Edward Foeller, Batavia; Dana Andrew Carlile, Webster; Jacob Michael Shmois, Rochester; Fugui He, Penfield; Stephen Albert Mruczek, Rochester, all of N.Y.

[73] Assignee: Eastman Kodak Company, Rochester, N.Y.

[21] Appl. No.: 610,018

[22] Filed: Mar. 4, 1996

[51] Int. Cl.⁶ .................................................. A61L 2/00
[52] U.S. Cl. ........................ 422/294; 422/295; 422/296; 422/302; 422/81; 206/532; 220/202; 220/260; 220/277; 222/80; 222/81; 222/82
[58] Field of Search ............................ 922/295, 294, 922/296, 298, 302, 305, 307, 81, 100, 113, 115, 118; 206/532; 220/202, 260, 277; 222/80, 81, 82; 225/93; 234/39

[56] References Cited

U.S. PATENT DOCUMENTS

| | | | |
|---|---|---|---|
| 2,888,542 | 5/1959 | Mork | 219/10.55 |
| 4,435,194 | 3/1984 | Picard et al. | 55/96 |
| 4,614,514 | 9/1986 | Carr | 604/113 |
| 4,781,898 | 11/1988 | Jones | 422/295 |
| 4,811,611 | 3/1989 | Uffenheimer | 73/864.22 |
| 5,019,344 | 5/1991 | Kutner et al. | 422/21 |
| 5,019,359 | 5/1991 | Kutner et al. | 422/294 |
| 5,039,495 | 8/1991 | Kutner et al. | 422/299 |
| 5,209,902 | 5/1993 | Matthews et al. | 422/21 |
| 5,215,715 | 6/1993 | Haswell et al. | 422/81 |
| 5,223,229 | 6/1993 | Brucker | 422/116 |
| 5,246,674 | 9/1993 | Katschnig et al. | 422/302 |
| 5,262,049 | 11/1993 | Ferkany | 210/258 |
| 5,304,766 | 4/1994 | Baudet et al. | 219/687 |
| 5,316,954 | 5/1994 | Hupe et al. | 436/89 |
| 5,320,804 | 6/1994 | Zakaria et al. | 422/21 |
| 5,382,406 | 1/1995 | Kruger et al. | 422/28 |
| 5,407,641 | 4/1995 | Katschnig et al. | 422/107 |
| 5,411,712 | 5/1995 | Woodmansee et al. | 422/186 |
| 5,424,047 | 6/1995 | Zwingenberger et al. | 422/296 |

FOREIGN PATENT DOCUMENTS

WO 93/18798  9/1993  WIPO.

*Primary Examiner*—Christopher Kim
*Attorney, Agent, or Firm*—William F. Noval

[57] ABSTRACT

Apparatus for heating and venting a container. The apparatus has a heating station for the container. A heater is disposed to supply heat to the heating station. A drive has a body and a reciprocable member. The body is mounted in predetermined relation to the receiving station. The reciprocable member is movable relative to the receiving station between a first position and a second position. A cannula is joined to the reciprocable member. The cannula has a hollow bore. The cannula is movable between a retracted position and an extended position by movement of the reciprocable member between the first position and the second position. A vent line communicates with the bore and the ambient environment.

12 Claims, 4 Drawing Sheets

APPARATUS FOR HEATING AND VENTING A CONTAINER

CROSS-REFERENCE TO RELATED APPLICATION

This application is related to a U.S. patent application, entitled "METHOD FOR HEATING AND VENTING A CONTAINER", filed by Ken Corby, Dave Foeller, Dana Carlile, Jacob Shmois, Fugui He, and Steve Mruczek, concurrently with this application; which application is hereby incorporated by reference herein.

This application is related to a U.S. patent application, entitled "PRESSURE LOCK ASSEMBLY AND PRESSURE VESSEL", filed by Dana Carlile, Dave Foeller, and Ken Corby, concurrently with this application; which application is hereby incorporated by reference herein (referred to hereafter as "SECOND INCORPORATED PATENT REFERENCE").

1. Field of the Invention

The invention relates to apparatus for heating and for releasing pressure, and more particularly relates to an apparatus for heating and venting a container.

2. Background of the Invention

It is known to sterilize articles such as re-usable dental and medical equipment between uses by exposing them to steam for a suitable length of time. It is also known that increasing the pressure of the steam in contact with the instruments and with the organisms to be denatured can reduce substantially the time required to achieve sterility and can improve the effectiveness of the process by increasing the temperature of the steam above that achievable at atmospheric pressure. Thus, large commercially-available steam autoclaves can operate at steam pressures of several atmospheres and temperatures in the range of 135° C. and higher. Generally, such devices can vent pressurized steam safely at the end of the sterilizing period through conventional valving to the exterior of the room or building in which they are located, permitting access to the sterilized tools soon after completion of sterilization.

More recently, relatively small devices have been proposed for sterilizing small medical instruments, for example, scalpels, dental handpieces, and drill burrs in doctors'and dentists'offices. These devices are essentially miniature autoclaves, small enough to fit on a bench top or desk. Typically, instruments to be sterilized are sealed in a flexible pouch containing a few milliliters of water or specialized disinfecting solution. The pouch may be enclosed in a pressure-resistant container, or cassette, and the water then heated to a boil to produce a steam atmosphere within the cassette. Further heating of the water can increase the steam pressure within the pouch to several atmospheres, and sterilization of the instruments can be complete within a few minutes. Heating may be caused, for example, by conventional thermal conduction and radiation in a conventional oven, or by microwave irradiation in a microwave oven.

U.S. Pat. Nos. 5,019,344 issued May 28, 1991; 5,019,359 issued May 28, 1991; and 5,039,495 issued Aug. 13, 1991, all issued to Kutner et al., disclose small-scale autoclaving. Instruments and liquid sterilant solution are introduced into a collapsible pouch formed of vapor-impermeable sheet material, the pouch is sealed to form a gas-tight assembly, and the assembly is heated to vaporize the solution to produce a pressurized atmosphere of hot sterilant vapor. In one embodiment, the pouch is irradiated with microwave radiation to cause the solution to boil.

PCT Application WO 93/18798 published Sep. 30, 1993, filed by Kutner et al. discloses proposed apparatus and method for sterilization comprising a gas-tight pouch assembly which is further contained within, and constrained by, a pressure-resistant enclosure which is at least partially formed of a material that is substantially transparent to microwave radiation. As in the above-cited disclosures, steam at supra-atmospheric pressure is created within the pouch and acts to denature organisms therein.

U.S. patent application Ser. No. 08/222,211 filed Apr. 4, 1994 by Corby et al. discloses an enclosure containing a pouch for steam sterilization of medical tools. Water in the pouch is boiled by application of microwave radiation.

A problem common to such prior devices is the presence of high-temperature steam at elevated pressure within the pouch at the conclusion of sterilization, at which time it may be desirable to recover the tools quickly from the pouch in order to place them back into service or to begin sterilizing another batch of contaminated tools. Implicit in these devices is the assumption that the device will be allowed to cool until the steam vapor condenses and the internal pressure matches the external atmospheric pressure, which can require several tens of minutes or more.

It is therefore desirable to provide an improved apparatus in which depressurization is accomplished conveniently and without a long waiting period, reducing overall cycle time and increasing system throughput.

SUMMARY OF THE INVENTION

The invention is defined by the claims. The invention, in its broader aspects, provides an apparatus for heating and venting a container. The apparatus has a heating station for the container. A heater is disposed to supply heat to the heating station. A drive has a body and a reciprocable member. The body is mounted in predetermined relation to the receiving station. The reciprocable member is movable relative to the receiving station between a first position and a second position. A cannula is joined to the reciprocable member. The cannula has a hollow bore. The cannula is movable between a retracted position and an extended position by movement of the reciprocable member between the first position and the second position. A vent line communicates with the bore and the ambient environment.

It is an advantageous effect of at least some of the embodiments of the invention that an improved apparatus is provided in which depressurization is accomplished conveniently and without a long waiting period, reducing overall cycle time and increasing system throughput.

BRIEF DESCRIPTION OF THE FIGURES

The above-mentioned and other features and objects of this invention and the manner of attaining them will become more apparent and the invention itself will be better understood by reference to the following description of embodiments of the invention taken in conjunction with the accompanying figures wherein.

DESCRIPTION OF PARTICULAR EMBODIMENTS

The apparatus of the invention is utilized by first placing an enclosed container within an oven chamber; the contents of the container are heated, preferably by microwave radiation; the container is then punctured; and gaseous by-products of the heating are vented to the exterior of the oven chamber. During the process, from heating, through puncturing and venting; the container is isolated from the user, within the oven chamber. In a preferred embodiment of the invention, the gaseous by-products are condensed to provide a liquid waste product, which can be readily captured for disposal.

Figure 7:
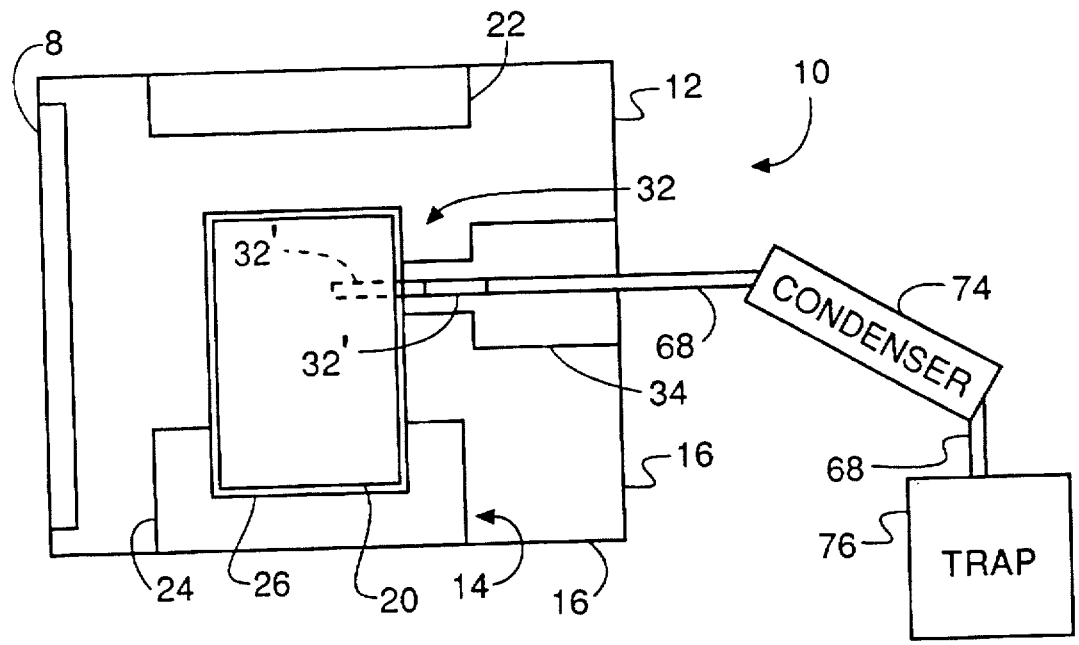
FIG. 7 is a semi-diagrammatical view of the apparatus of the invention.

Referring now particularly to FIG. 7, the apparatus 10 of the invention has an oven chamber 12 than includes a heating station 14. The oven chamber 12 has walls 16 and a door 18 which can be opened to permit access to the interior of the oven chamber 12 for loading. In preferred embodiments of the invention, the oven chamber 12 provides full enclosure when the door 18 is closed and the container 20 cannot be removed from the oven chamber 12 until the container 20 has been vented or vented and cooled. An actuable cannula assembly 21 is located in the oven chamber 12.

The apparatus 10 includes a heater 22 that supplies heat to the container 20 retained in the heating station 14. The heater 22 can take a variety of forms, but it is preferred that the heater 22 be a microwave heating element. Detailed characteristics of the heater 22, for example, location in the apparatus, power requirements, and the like, are well known to those of skill in the art. For example, the oven chamber 12 and heater 22 can be those of a commercial microwave oven.

The term "heating station" is used broadly herein to refer to one or more structures in the oven chamber 12 that retain the container 20 in a particular location (hereafter also referred to as "container site") within the oven chamber 12. It is preferred that the location not be variable, while the apparatus 10 is in use, since this allows other components of the apparatus to be positioned relative to the fixed container site. The nature of the structures used for the heating station 14 can vary widely depending upon the nature of the container 20 used. The heating station 14 must locate the container 20 within the oven chamber 12, that is, retain the container 20 in place such that it can be both heated and punctured. If the container 20 is substantially rigid, then the heating station 14 can be configured to simply hold the container 20 in place. If the container 20 can flex, or expand or inflate during use, then the heating station 14 must both hold the container 20 in place and define the "shape" of the container 20, that is, define the location of the container 20 relative to other components of the apparatus 10. For example, FIG. 7 schematically illustrates an embodiment of the invention in which the heating station 14 has a support 24 and a removable cassette 26. The container 20 is a flexible and expandable polymeric pouch. This kind of cassette 26 and pouch 20 is further illustrated (in part) in FIGS. 5–6. The cassette 26 has clamshells 28 pivotable about a hinge 29 and held together opposite the hinge 29 by a latch or the like (not shown). The clamshells 28 define an interior 30 configured to hold a flexible container or pouch 20. The pouch 20 can be loose within the interior 30 or can have peripheral portions (not illustrated) pinched between the clamshells 28 to hold the pouch 20 in place. Suitable cassettes 26 and pouches 20 are known to those of skill in the art, with the exception that the cassette 26 must be ported to receive the cannula, as discussed below in greater detail.

Referring now to FIGS. 1–3 and 5–6, the actuable cannula assembly 21 includes a cannula or needle 32 and a drive or motive unit 34. The cannula 32 is a hollow tube having a free end 36, a secured end 38, and a barrel 40 extending between the two ends. The barrel 40 has a hollow bore 41. The needle 32 can have a variety of configurations depending upon the characteristics of the containers to be vented. In currently preferred embodiments of the invention, the cannula 32 is configured for puncturing flexible polymeric containers. In these embodiments of the invention, the free end 36 is pointed, so as to more readily puncture the container 20 without tearing. It is desirable in these embodiments, that, after puncturing, a seal be present between the barrel 40 of the cannula 32 and the container 20. Although an additional sealing member (not illustrated) could be provided to overlap the cannula 32 and site of puncture, it is more desirable that the seal be provided by engagement of the container itself and the cannula around the site of puncture.

The free end 36 can have a variety of pointed configurations. In one configuration, the cannula 32 is shaped like a hospital-type syringe needle and is a constant diameter tube that is angled at the end by one or more cuts and is sharpened. It has been determined, however, that this configuration is not optimal, in that a non-circular hole is produced that does not provide a seal to the cannula and leakage tends to occur during venting.

Figure 8:
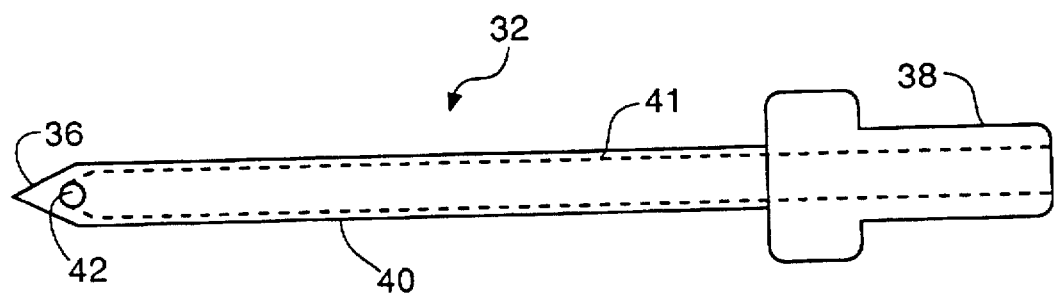
FIG. 8 is a side plan view of the cannula of the actuable cannula assembly of FIG. 1.
Figure 9:
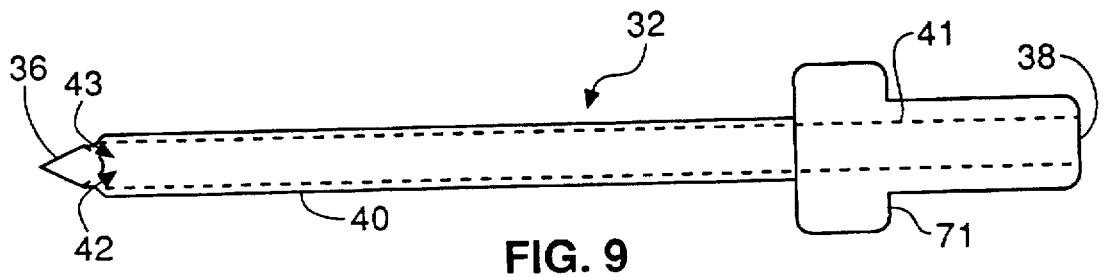
FIG. 9 is a top plan view of the cannula of the actuable cannula assembly of FIG. 1.

In a preferred embodiment of the invention, the cannula 32 has a cone-shaped end 36 that narrows to a point. The axial bore 41 ends in spaced relation to the point and one or more transverse passages 42 extend laterally outward from the bore 41 to the exterior. Referring now to FIGS. 8–9, in a currently preferred embodiment of the invention, the cone-shaped free end 36 (a right cone having a cone angle of about 40 degrees) has a pair of inlet passages 42 opening outward onto the free end 36 in spaced relation to both the apex of the free end 36 and the barrel 40. Each passage intersects the barrel 40 at an angle of about 45 degrees.

The drive 34 has a body 44 and a reciprocable member 46. The body 44 is mounted in predetermined relation to the heating station 14 and the reciprocable member 46 is movable relative to the heating station 14 between a first position 48 (shown in FIG. 5) and a second position 50 (shown in FIG. 6). The secured end 38 of the cannula 32 is joined to the reciprocable member 46. The cannula 32 is moved between a retracted position 52 (shown in FIG. 5 and indicated by solid lines in FIG. 7) and an extended position 54 (shown in FIG. 6 and indicated by solid lines in FIG. 7) by the movement of the reciprocable member 46 between the first and second positions 48,50, respectively. In the retracted position 52, the cannula 32 is displaced from the heating station or container site 14. In the extended position 54, the cannula 32 extends into the container site 14. A container 20, present in the container site 14 while the cannula 32 is moved from retracted position 52 to extended position 54, is punctured by the cannula 32. The cannula 32 extends into the container 20 sufficiently that the bore 41 of the cannula 32 is in communication with the interior 30 of the container 20.

Figure 5:
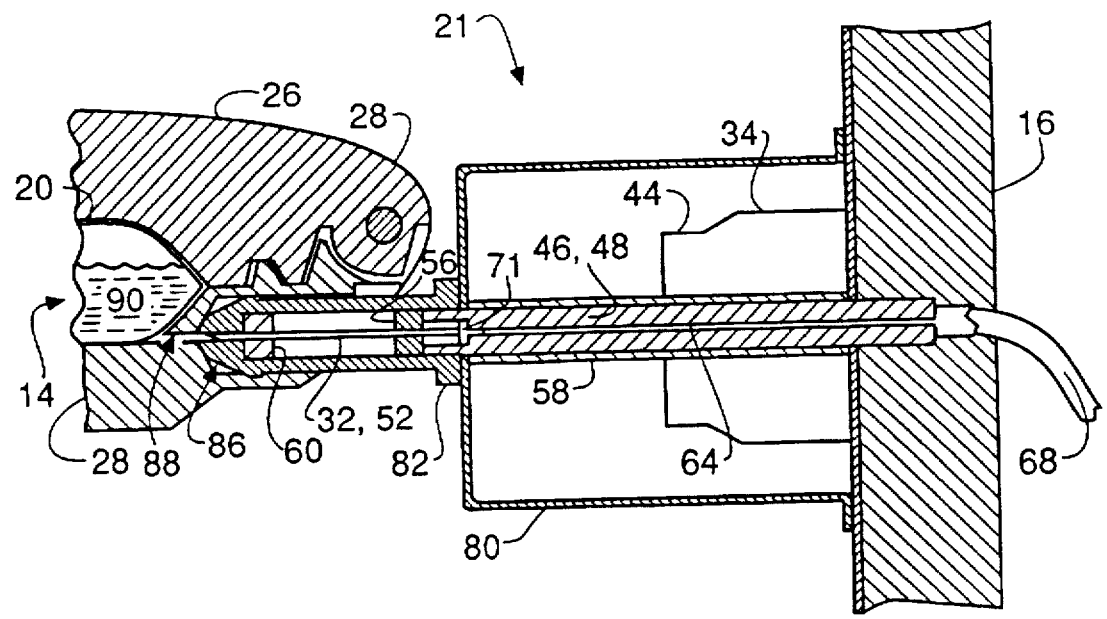
FIG. 5 is a partial cross-sectional view of an embodiment of the apparatus of the invention utilizing the actuable cannula assembly of FIG. 3. The cannula is shown in a retracted position.
Figure 6:
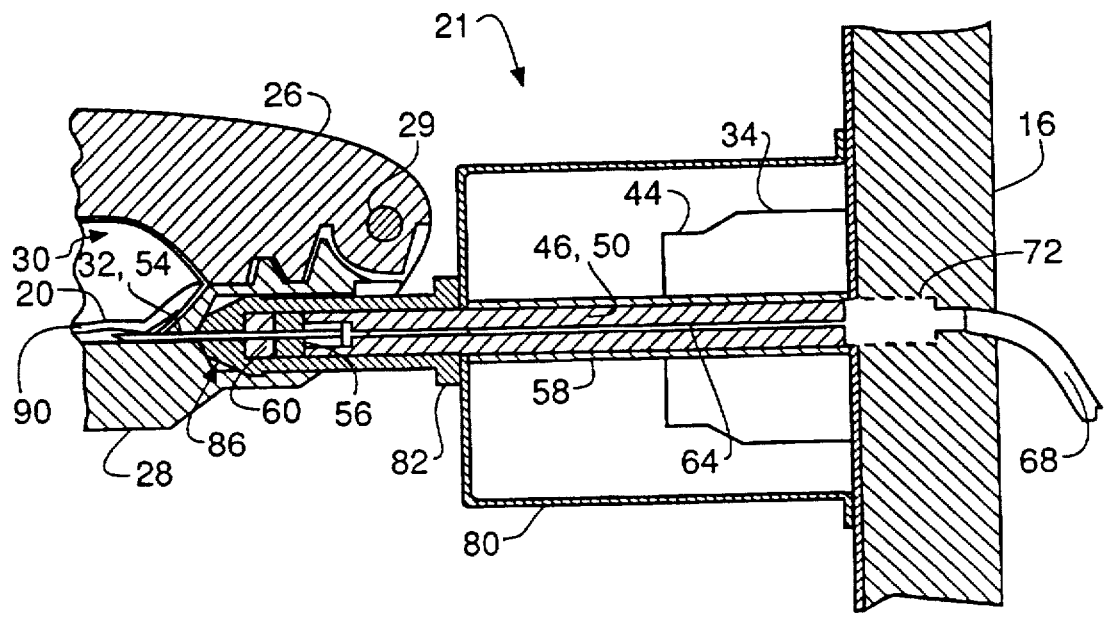
FIG. 6 is the same view as FIG. 5, but the cannula is in an extended position.

In preferred embodiments of the invention, as shown in FIGS. 5–6, the cannula 32 enters the container 20 in a direction substantially perpendicular to the container surface, so as to minimize both the size of the puncture hole to prevent leakage and to minimize any risk of tearing or disrupting the container. The drive 34, in these embodiments, is a "linear drive", that is, the drive 34 moves the cannula 32 between retracted and extended positions 52,54 along a line coaxial with the longitudinal dimension of the cannula 32, and substantially precludes movement of the cannula 32 in directions transverse to that line. The linear drive can provide for rotation of the cannula 32 about the axis of the barrel 40, however, this is not currently preferred.

The actuable cannula assembly 21 can include one or more guides to help ensure desired motion of the cannula 32 and reciprocable member 46. In the embodiment of the invention shown in the Figures, guides includes a slide bushing 56 fixed to the cannula 32 and a guide cylinder 58, within which the slide bushing 56 moves. The guide cylinder 58 includes a stop 60 at its outer end which limits travel of the slide bushing 56 and cannula 32. One or more additional bushings can be provided in the cylinder 58 or on the cannula 32 as desired.

Figure 1:
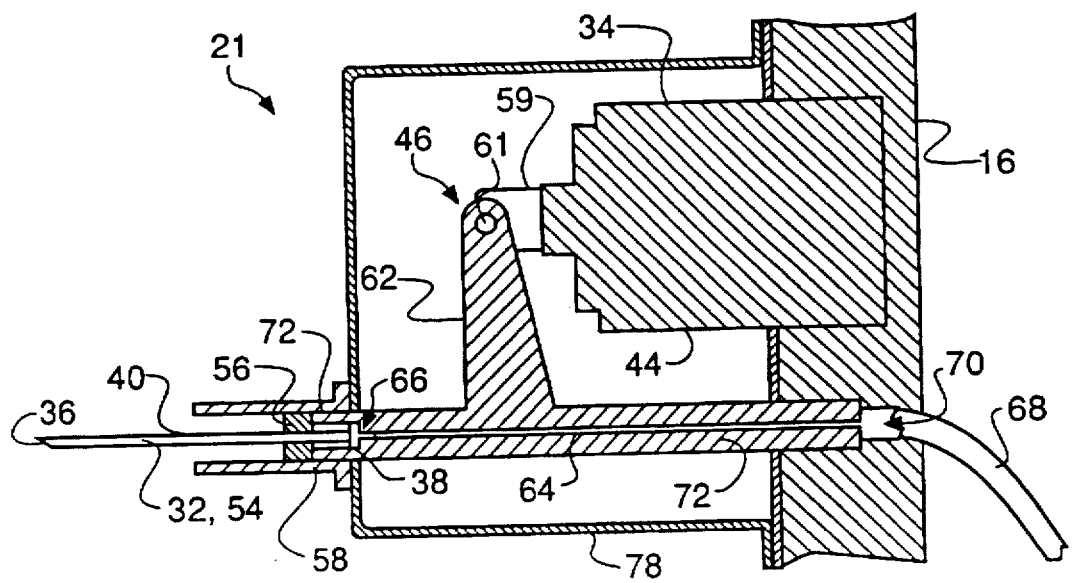
FIG. 1 is a vertical cross-sectional view through the actuable cannula assembly of an embodiment of the apparatus of the invention.

The drive 34 can be powered by a motive unit or can be manually operated by the user. A powered drive is highly preferred. Suitable motive units include electric solenoids, pneumatic cylinders, and hydraulic cylinders. The reciprocable member can be the slug or cylinder or the like of the motive unit (also referred to hereafter as an internal reciprocating member), as in FIGS. 2, 3, 5, and 6, or can comprise the slug or cylinder or the like and one or more additional structures, to which the cannula is mounted (also referred to hereafter as an external reciprocating member). FIG. 1 illustrates an external reciprocating member in which the slug 59 is mounted via a pivot 61 to a slider 62. An internal reciprocating member can be more compact than a similar external reciprocating member. In either case, the reciprocable member 46 includes an internal passage 64 that communicates with the bore 41 of the cannula 32 at an inflow port 66 and with a vent line 68 at an outflow port 70.

Movement of the reciprocable member 46 is accommodated by providing slack in the vent line 68 to permit movement of an end of the vent line 68 with the reciprocable member 46 or by sliding movement of the reciprocable member within a socket communicating with the vent line (as shown in FIG. 1) or by use of a telescoping connection (not shown) or the like. The reciprocable member 46 can be joined to the cannula 32 and vent line 68 by any convenient means, such as, press fit, adhesive, reciprocal threads, bayonet mount or the like. In the embodiments shown in the Figures, the secured end 38 or the cannula 32 has a shoulder 71 which fits within and is tightly engaged by the tube-shaped inflow port 66 of the reciprocable member 46. The outflow port 70 is slideably engaged by one end a socket or connector 72 formed in part of a wall 16 of the oven chamber 12. The vent line 68 is press fit within the other end of the socket 72.

The vent line 68 communicates with the ambient environment, preferably through a condenser 74 and trap or condensate receiver 76. The condenser 74 need not be complex and can simply be a lengthened portion of the vent line 68, if the ambient environment can provide sufficient cooling.

The cannula 32 and drive 34 are mounted in the immediate vicinity of the container site 14. If heat is supplied to the container, by radiation, or conduction, or convection; the mounting of the components is very straight-forward; but provision must be made for use of components that can withstand heat or for insulation or the like to reduce component heating. If heat is supplied by microwave radiation, then shielding must be provided or components must be used that will withstand unshielded exposure to microwaves without arcing. Cannulas can be formed from glass or plastic for unshielded exposure to microwaves; however, metal cannulas have been found preferable for reasons of strength, durability, resistance to breaking, and retention of sharpness with repeated use.

Figure 2:
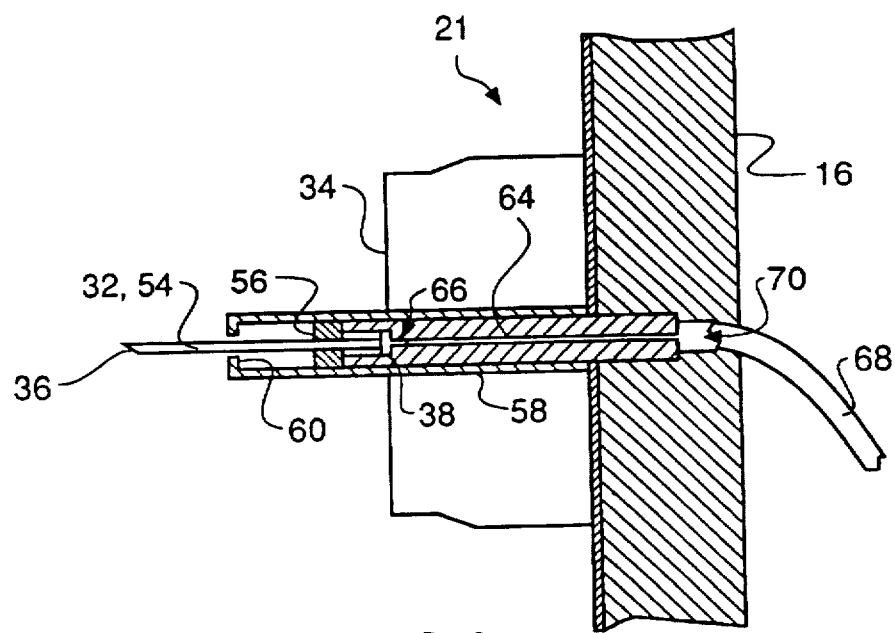
FIG. 2 is a vertical cross-sectional view through the actuable cannula assembly of a second embodiment of the apparatus of the invention.
Figure 3:
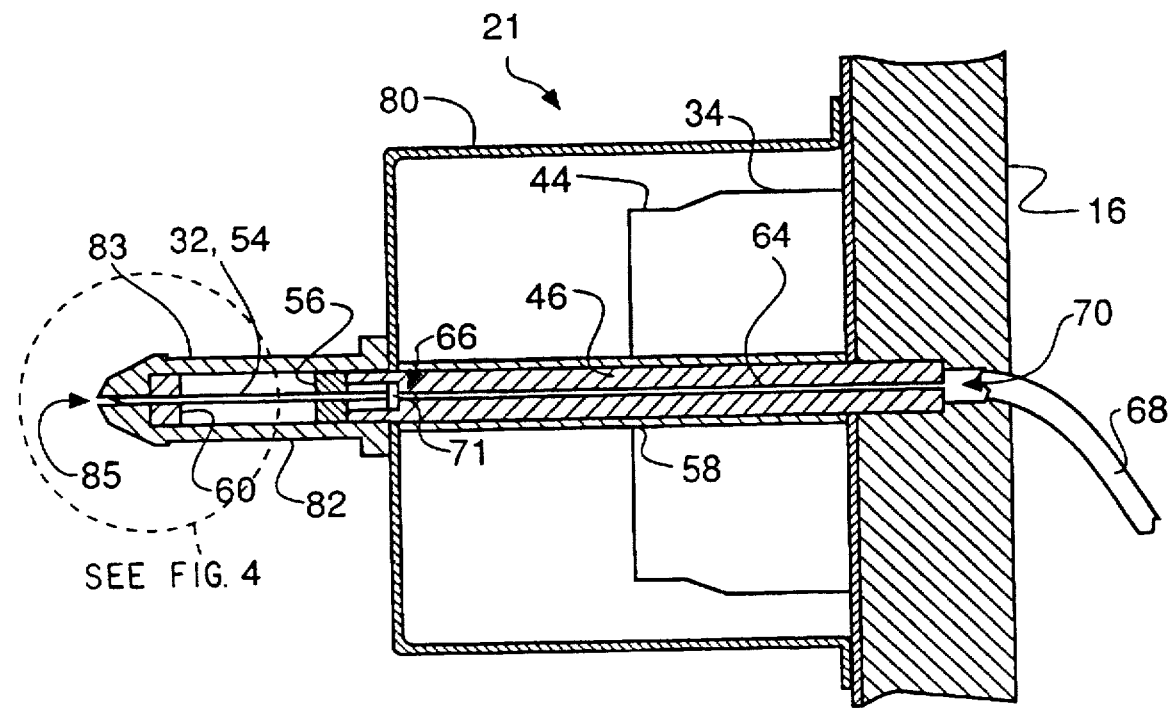
FIG. 3 is a vertical cross-sectional view through the actuable cannula assembly of a third embodiment of the apparatus of the invention.

Actuable cannula assemblies 21 for use with non-microwave heating or microwave heating with non-arcing components, are shown in FIGS. 1 and 2. In FIG. 1, the motive unit 34 is attached to a wall 16 of the oven chamber 12 and a bracket 78, also attached to a wall 16 of the oven chamber 12, supports guide cylinder 58. In FIG. 2, the guide cylinder 58 is attached to the motive unit 34, which is attached to wall 16. Wall 16 is illustrated by a two layer structure. The walls 16 of the oven chamber 12 can have a variety of configurations, with one or more layers of various kinds, as is well known to those of skill in the art. For example, the wall shown in FIG. 1 and 2 could have a conductive metal inner layer backed by a support layer of a different material.

The embodiments of FIGS. 1 and 2 are unsuited to use of a conductive cannula in an environment which may include exposure to microwave energy. Even if the cannula is grounded, transient inequalities in the strength of the microwave field can create large instantaneous potentials on the cannula tip, leading to arcing discharge and damage to the tip.

Referring now to FIGS. 3–6, in embodiments of the invention that utilize microwave heating, the drive 34 is shielded from radiation emitted by the microwave heating element 22. The cannula 32 is shielded from microwave radiation when the cannula 32 is in the retracted position 52. The cannula 32 is unshielded from radiation emitted by the microwave heating element 22 when the cannula 32 is in the extended position 54, but the microwave source 22 is provided with an interlock that prevents the microwave source 22 from operating when the cannula 32 is in the extended position 54. The details of such interlocks are well known to those of skill in the art, since similar interlocks are provided for the doors of conventional microwave ovens to prevent operation when the door is open.

Figure 4:
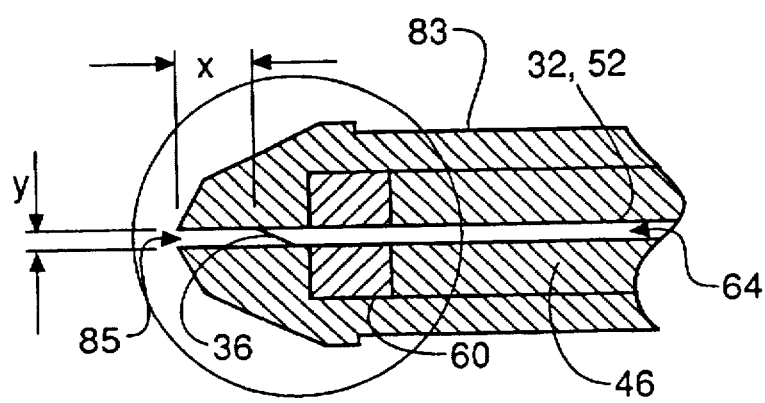
FIG. 4 is a partial enlargement of the area of FIG. 3 indicated by circle 4.

Shielding can be provided by recessing the actuable cannula assembly 21 within a wall 16 of the oven chamber (not shown) or by the use of discrete shielding. Referring now to the embodiment of FIGS. 3, 4, 5, and 6, the drive 34 is mounted to the wall 16 and a drive shield 80, also mounted to the wall 16 is provided over the drive 34. The drive shield 80 is formed of an electrically-conductive material and is, in effect, outside the oven chamber 16. In this embodiment of the invention, guide 58 includes a cannula shield 82, that is electrically conducting and is electrically grounded to the drive shield 80. Referring now particularly to FIG. 4, the cannula shield 82 has a forward portion 83 that includes a bushing 84 that closely engages the cannula 32 in slideable relation. The forward portion 83 has an opening 85 that communicates with the interior of the oven chamber 12. The cannula 32 extends through the opening 85, when the cannula 32 is in the extended position 54 and is set back from the opening 85 when the cannula 32 is in the retracted position 52.

The dimensions of the cannula shield 82 are such that microwave radiation is excluded from the cannula 32 when the cannula 32 is in the retracted position 52. In an embodiment of the invention in which the microwave source 22 produces microwave radiation at 2450 megahertz, the end 36 of the cannula 32 is recessed from the opening 85 by a distance "x" equal to at least 1.5 times the diameter of the cannula 32 and the opening 85 has a diameter "y" of less than about 4.59 mm.

Referring now to FIGS. 5–6, in a particular embodiment of the invention, the apparatus 10 includes a pressure resistant cassette 26 that holds the pouch 20 and mates with the forward portion of the cannula shield 82. A suitable cassette 26 for this purpose is generally similar to the cassette disclosed in the "SECOND INCORPORATED PATENT REFERENCE". The cassette 26 swings open to receive the container 20 and then closes and locks in place.

A cassette 26 suitable for use in the apparatus 10 of the invention, has a port 86 that is complementary in shape to the cannula shield 82. The port 86 closely engages the cannula shield 82. The cassette 26 is preferably removable from the oven chamber 12 for loading and unloading. The port 86 of the cassette 26 is slideable on and off the cannula shield 82 for removal and reattachment. The port 86 includes a hole or accessway 88 that is aligned with the opening 85 of the cannula shield 82. The cannula 32, when in the extended position 54, extends through the hole 88 and into the container site 14 (in this embodiment, the interior of the cassette 26). When in use, a flexible container or pouch 20, within the cassette 26, is held within the container site 14 by internal pressure within the container 20. The container 20 may contain, for example, small medical instruments (not shown) being autoclaved by superheated steam at elevated temperature and pressure, for example, 135° C. at 35–55 psi (4 bars). The steam is produced from water supplied within the container 20.

The material of the container 20 is sufficiently strong that it bridges the hole 88 without bursting under the working load, but is sufficiently weak to puncture when engaged by the cannula 32 under the same load. The hole 88 is slightly larger in diameter than the cannula 32. The cannula 32 can be sized to accommodate a particular pouch or container 20. Assuming uniform barrel wall thickness, a cannula 32 having a larger exterior diameter will drain a container 20 more quickly than a smaller diameter cannula. On the other hand, the smaller diameter cannula 32 will require a smaller hole 88 that must be bridged by the material of the pouch 20. By simple experimentation, a suitable combination of cannula diameter and container material strength can be readily determined. A currently preferred cannula exterior diameter is about 2.5 mm.

The apparatus can include a controller (not separately illustrated) to monitor and control either the temperature or pressure in the container during sterilization or other pressure treatment. The heat source is actuated and deactuated by the controller as needed to meet predetermined limits. The apparatus can alternatively be controlled by a relief valve in communication with the interior of the container. In this alternative, temperatures are not necessarily monitored or controlled.

The controller can also be used to interlock the door against opening during heating, venting, and cooling (if desired). Controllers and interlock mechanisms are well known for microwave ovens. The controller can also provide one or more signals to actuate the motive unit and move the cannula between retracted and extended positions. For example, if the motive unit is a solenoid, the cannula is moved from retracted to extended position by energizing and from extended to retracted position by deenergizing.

In use, a container 20 is loaded into the station 14 and the oven chamber 12 is closed. The contents of the container 20 are to be heated and, with heating, produce vaporous by-products. The contents of the container are typically water or sterilization media 90 and articles to be sterilized (not illustrated). Treating conditions within the container 20 are such that the vaporous by-products are contained under elevated pressure. After a desired time period, the heating is discontinued. The cannula 32 is then moved by the drive 34 from the retracted position 52 to the extended position 54. This movement causes the cannula 32 to puncture and penetrate the wall of the container 20. A seal can be provided between the container 20 and the cannula 32. This seal is preferably a result of the material of the container deforming about the barrel 40 of the cannula 32. Pressure within the container 20 causes fluid contents of the container 20 to travel through the cannula 20 and out through the vent line 68. Gravity can also assist in draining of the container 20. In a preferred embodiment of the invention, the cannula 32 is at the lowest point in the container 20 and pressurized vapor drives out substantially all the liquid in the container 20 prior to escape of the vapor. After venting is completed, the cannula 32 is withdrawn from extended position 54 to retracted position 52. The container 20, no longer under pressure, may then be removed, or may be retained for further cooling and then removed.

While specific embodiments of the invention have been shown and described herein for purposes of illustration, the protection afforded by any patent which may issue upon this application is not strictly limited to a disclosed embodiment; but rather extends to all modifications and arrangements which fall fairly within the scope of the claims which are appended hereto:

list
apparatus 10
oven chamber 12
heating station or container site 14
walls 16
door 18
container or pouch 20
actuable cannula assembly 21
heater 22
support 24
cassette 26
clamshells 28
hinge 29
interior 30
cannula 32
drive or motive unit 34
free end 36
secured end 38
barrel 40
bore 41
transverse passages 42
body 44
reciprocable member 46
first position 48
second position 50 retracted position 52
extended position 54
slide bushing 56
guide cylinder 58
slug 59
stop 60
slider 62
internal passage 64
inflow port 66
vent line 68
outflow port 70
shoulder 71
socket or connector 72
condenser 74
trap or condensate receiver 76
bracket 78
drive shield 80
cannula shield 82
forward portion 83
bushing 84
opening 85
port 86
hole or accessway 88

What is claimed is:

1. Apparatus for heating and venting a container, said apparatus comprising:

a heating station for said container;

a heater disposed to supply heat to said heating station;

a drive having a body and a reciprocable member, said body being mounted in predetermined relation to said receiving station, said reciprocable member being movable relative to said receiving station between a first position and a second position;

a cannula joined to said reciprocable member, said cannula having a hollow bore, said cannula being movable between a retracted position and an extended position by movement of said reciprocable member between said first position and said second position; and a vent line communicating with said bore and the ambient environment.

2. The apparatus of claim 1 wherein said vent line includes a condenser and a condensate receiver.

3. The apparatus of claim 1 wherein said cannula in said extended position is disposed at the lowest point of said heating station.

4. The apparatus of claim 1 wherein said heater is a microwave heating element.

5. The apparatus of claim 4 wherein said drive is shielded from said microwave heating element.

6. The apparatus of claim 5 wherein said cannula is shielded from said microwave heating element when said cannula is in said retracted position and is unshielded from said microwave heating element when said cannula is in said extended position.

7. Apparatus for heating and venting a container, said apparatus comprising:

an enclosure having a plurality of walls, said enclosure defining a microwave chamber;

a microwave source disposed in operative relation to said microwave chamber;

a drive having a body and a reciprocable member, said reciprocable member being movable relative to said receiving station between a first position and a second position, said drive being shielded from said microwave source;

a cannula having a free end, a secured end, and a hollow bore, said secured end being joined to said reciprocable member, said cannula being movable between a retracted position and an extended position by movement of said reciprocable member between said first position and said second position, said free end being disposed in said microwave chamber when said said cannula is in said extended position;

a cannula shield disposed to shield said cannula from said microwave source when said cannula is in said retracted position; and a vent line communicating with said bore and the ambient environment.

8. The apparatus of claim 7 wherein said cannula shield has a forward portion engaging said cannula in slideable relation, said forward portion having an opening communicating with said microwave chamber, and wherein said cannula extends through said opening when said cannula is in said extended position and said cannula is recessed from said opening when said cannula is in said retracted position.

9. The apparatus of claim 8 wherein said cannula is recessed from said opening by a distance equal to at least 1.5 times the diameter of said cannula.

10. The apparatus of claim 9 wherein said opening is less than about 4.6 mm in diameter.

11. The apparatus of claim 7 wherein said enclosure further comprises a removable cassette holding said container, said cassette having a port disposed in mating relation with said cannula shield.

12. The apparatus of claim 11 wherein said port has a hole aligned with said cannula.

* * * * *